United States Patent
Fleming et al.

[19]

[11] Patent Number: 6,132,388
[45] Date of Patent: Oct. 17, 2000

[54] GUIDE WIRE TIP

[75] Inventors: Thomas E. Fleming, Plymouth; Jeffrey H. Vogel, Brooklyn Park, both of Minn.

[73] Assignee: SciMed Life Systems, Inc., Maple Grove, Minn.

[21] Appl. No.: 08/953,865

[22] Filed: Oct. 16, 1997

[51] Int. Cl.[7] .................................................. A61B 5/00
[52] U.S. Cl. ........................................................ 600/585
[58] Field of Search ................................. 600/433–435, 600/585

[56] References Cited

U.S. PATENT DOCUMENTS

| | | | |
|---|---|---|---|
| 3,749,086 | 7/1973 | Kline et al. | 128/2 |
| 3,906,938 | 9/1975 | Fleischhacker | 128/2 |
| 4,282,876 | 8/1981 | Flynn | 128/349 |
| 4,345,602 | 8/1982 | Yoshimura et al. | 128/349 |
| 4,456,017 | 6/1984 | Miles | 128/772 |
| 4,534,363 | 8/1985 | Gold | 128/772 |
| 4,538,622 | 9/1985 | Samson et al. | 128/772 |
| 4,545,390 | 10/1985 | Leary | 128/772 |
| 4,554,929 | 11/1985 | Samson et al. | 128/772 |
| 4,619,274 | 10/1986 | Morrison | 128/772 |
| 4,642,267 | 2/1987 | Creasy et al. | 428/413 |
| 4,682,607 | 7/1987 | Vaillancourt et al. | 128/772 |
| 4,719,924 | 1/1988 | Crittenden et al. | 128/772 |
| 4,721,117 | 1/1988 | Mar et al. | 128/772 |
| 4,724,846 | 2/1988 | Evans, III | 128/772 |
| 4,729,914 | 3/1988 | Kliment et al. | 428/36 |
| 4,739,768 | 4/1988 | Engelson | 128/658 |
| 4,748,986 | 6/1988 | Morrison et al. | 128/772 |
| 4,763,647 | 8/1988 | Gambale | 128/657 |
| 4,811,743 | 3/1989 | Stevens | 128/772 |
| 4,813,434 | 3/1989 | Buchbinder et al. | 128/772 |
| 4,830,023 | 5/1989 | de Toledo et al. | 128/772 |
| 4,835,003 | 5/1989 | Becker et al. | 427/2 |
| 4,846,186 | 7/1989 | Box et al. | 128/657 |
| 4,846,193 | 7/1989 | Tremulis et al. | 128/772 |
| 4,867,173 | 9/1989 | Leoni | 128/772 |
| 4,867,174 | 9/1989 | Skribiski | 128/772 |
| 4,884,579 | 12/1989 | Engelson | 128/772 |
| 4,899,787 | 2/1990 | Ouchi et al. | 138/131 |
| 4,922,924 | 5/1990 | Gambale et al. | 128/772 |
| 4,925,445 | 5/1990 | Sakamoto et al. | 604/95 |
| 4,934,380 | 6/1990 | de Toledo | 128/772 |
| 4,955,862 | 9/1990 | Sepetka | 604/164 |
| 4,961,731 | 10/1990 | Bodicky et al. | 604/264 |

(List continued on next page.)

FOREIGN PATENT DOCUMENTS

| | | |
|---|---|---|
| 0 340 304 A1 | 11/1989 | European Pat. Off. . |
| 0 380 102 A1 | 8/1990 | European Pat. Off. . |
| 0 395 098 A1 | 10/1990 | European Pat. Off. . |
| 0 405 823 A2 | 1/1991 | European Pat. Off. . |
| 0 407 965 A1 | 1/1991 | European Pat. Off. . |
| 0 739 641 A1 | 10/1996 | European Pat. Off. . |
| 2 401 668 | 8/1977 | France . |
| 60-12069 | 1/1985 | Japan . |
| 2-180277 | 7/1990 | Japan . |
| 8-257133 | 10/1996 | Japan . |
| WO 85/01444 | 4/1985 | WIPO . |
| WO 89 09626 | 10/1989 | WIPO . |
| WO 90/05486 | 5/1990 | WIPO . |
| WO 91/00051 | 1/1991 | WIPO . |
| WO 92/04072 | 3/1992 | WIPO . |
| WO 97/13455 | 4/1997 | WIPO . |

OTHER PUBLICATIONS

Tegtmeyer, "Current Problems in Diagnostic Radiology", vol. XVI, No. 2, Mar./Apr., 1987, 5 pages.

*Primary Examiner*—Max Hindenburg
*Attorney, Agent, or Firm*—Crompton, Seager & Tufte, LLC

[57] ABSTRACT

A guide wire tip including a core wire having a proximal end and a distal end. The core wire includes a tapered portion proximate the distal end. The tapered portion has a transverse, cross-sectional area which generally decreases distally. The tip is disposed at the distal end of the core wire. The tip has a transverse, cross-sectional area larger than the smallest transverse cross-sectional area of the tapered portion of the core wire. A coil extends over the core wire to the tip. The coil extends over at least a portion of the tapered portion. A radiopaque sheath is disposed proximate the tip and between the core wire and the coil.

10 Claims, 1 Drawing Sheet

U.S. PATENT DOCUMENTS

| | | | |
|---|---|---|---|
| 4,971,490 | 11/1990 | Hawkins | 128/772 |
| 4,977,901 | 12/1990 | Ofstead | 128/772 |
| 4,991,602 | 2/1991 | Amplatz et al. | 128/772 |
| 5,001,825 | 3/1991 | Halpern | 29/456 |
| 5,002,559 | 3/1991 | Tower | 606/194 |
| 5,037,391 | 8/1991 | Hammerslag et al. | 604/95 |
| 5,045,072 | 9/1991 | Castillo et al. | 604/280 |
| 5,054,501 | 10/1991 | Chuttani et al. | 128/772 |
| 5,060,660 | 10/1991 | Gambale et al. | 128/772 |
| 5,061,254 | 10/1991 | Karakelle et al. | 604/265 |
| 5,063,935 | 11/1991 | Gambale | 128/657 |
| 5,065,769 | 11/1991 | de Toledo | 128/772 |
| 5,067,489 | 11/1991 | Lind | 128/772 |
| 5,069,226 | 12/1991 | Yamauchi et al. | 128/772 |
| 5,078,702 | 1/1992 | Pomeranz | 604/280 |
| 5,095,915 | 3/1992 | Engelson | 128/772 |
| 5,129,890 | 7/1992 | Bates et al. | 604/281 |
| 5,135,503 | 8/1992 | Abrams | 604/164 |
| 5,144,959 | 9/1992 | Gambale et al. | 128/772 |
| 5,147,317 | 9/1992 | Shank et al. | 604/164 |
| 5,174,302 | 12/1992 | Palmer | 128/772 |
| 5,176,149 | 1/1993 | Grenouillet | 128/772 |
| 5,209,730 | 5/1993 | Sullivan | 604/96 |
| 5,211,636 | 5/1993 | Mische | 604/264 |
| 5,217,026 | 6/1993 | Stoy et al. | 128/772 |
| 5,228,453 | 7/1993 | Sepetka | 128/772 |
| 5,243,996 | 9/1993 | Hall | 128/772 |
| 5,259,393 | 11/1993 | Corso, Jr. et al. | 128/772 |
| 5,333,620 | 8/1994 | Moutafis et al. | 128/772 |
| 5,342,383 | 8/1994 | Thomas | 606/190 |
| 5,345,945 | 9/1994 | Hodgson et al. | 128/772 |
| 5,365,943 | 11/1994 | Jansen | 128/772 |
| 5,372,144 | 12/1994 | Mortier et al. | 128/772 |
| 5,409,015 | 4/1995 | Palermo | 128/772 |
| 5,411,476 | 5/1995 | Abrams et al. | 604/95 |
| 5,421,349 | 6/1995 | Rodriguez et al. | 128/772 |
| 5,452,726 | 9/1995 | Burmeister et al. | 128/772 |
| 5,507,301 | 4/1996 | Wasicek et al. | 128/772 |
| 5,533,985 | 7/1996 | Wang | 604/264 |
| 5,636,642 | 6/1997 | Palermo | 128/772 |
| 5,637,089 | 6/1997 | Abrams et al. | 604/95 |
| 5,666,969 | 9/1997 | Urick et al. | 128/772 |
| 5,788,654 | 8/1998 | Schwager | 600/585 |

GUIDE WIRE TIP

BACKGROUND OF THE INVENTION

The present invention relates in general to intraluminal medical devices, and more particularly to guide wire tips.

The use of intraluminal catheters for treatment of various medical problems within the body is well known. It is also well known that a variety of difficulties may be encountered as the catheter is steered through the selected lumen to a desired point within the body. The path may be tortuous and the point of interest may be difficult to locate precisely. To overcome these difficulties, a flexible guide wire may first be inserted into the vascular lumen to the desired location. Once a guide wire is in position, a desired catheter may then be slid over the guide wire to reach the desired situs in the body.

It can readily be seen that it is important to have a guide wire that is flexible enough to traverse the tortuous vascular system. It can also be readily seen that it is important to have a guide wire that is radioscopic such that the physician can verify the position or location of the guide wire within the vascular lumen.

A continuing series of technical improvements and additions have been made in the catheter field to provide devices and methods which can overcome certain of these difficulties. One such series of improvements has resulted in the now well known use of a thin flexible guide wire having a tapered distal section that can be more easily steered through the lumen by forces applied to a proximal section. Because the distal section of a tapered guide wire may lose pushability, another improvement that has been developed is the use of a coiled wire helix which is wrapped around the distal tapered section of the guide wire. The coiled wire helix may improve the pushability of the distal tapered section of the guide wire while maintaining overall flexibility.

An example of a guide wire having a coiled wire helix is disclosed in U.S. Pat. No. 4,619,274 issued to Morrison. Morrison discloses a core member having a proximal and a distal end wherein the core member has a decreasing cross sectional area in a direction toward the distal end. The decreasing cross sectional area is incremental in that the core member comprises a plurality of fixed diameter cylinders which are coupled together by tapered sections. The diameters of the fixed diameter cylinders become smaller in the direction of the distal end of the core member.

Morrison further discloses a tapered coil which is carried and secured to the core element and extends over the core element. The tapered coil has a proximal end and a distal end wherein the diameter of the tapered coil decreases toward the distal end. Furthermore, the coil is formed of wire having a diameter which decreases toward the distal end. The improvements suggested by Morrison may provide some increased pushability while maintaining a degree of flexibility. However, the decreasing diameter core member and tapered coil may limit the pushability of the distal tip of the core member.

Another example of a guide wire having a coiled wire helix is disclosed in U.S. Pat. No. 4,846,186 issued to Box et al. In Box et al., a core member having an initial uniform diameter segment tapers along a uniform portion to a second constant diameter segment. A flexible spring tip surrounds, and is attached to, the second constant diameter segment and extends distally therefrom. The core member again tapers in a region where the flexible spring separates from the core member. Within the flexible spring, a portion of the core member is flattened to increase the flexibility of the distal portion of the core member. The flattened core and spring are brazed together at an extreme distal tip portion to form a distal guide wire tip.

A further variant of a guide wire having a reduced diameter distal portion surrounded by a coil wire helix is disclosed in U.S. Pat. No. 4,538,622 to Samson et al. The guide wire disclosed in Samson et al. includes an elongated stainless steel core wire having a reduced diameter distal portion including two constant diameter portions and two tapered portions.

The reduced diameter distal portion is surrounded by a first proximately disposed coil and a second distally disposed coil. The proximate coil is preferably stainless steel and is soldered at its proximal end to the core wire. The distal coil is preferably formed from a radiopaque material such as gold or platinum to allow location of the distal end of the guide wire by fluoroscopy. Under a fluoroscope, the radiopaque coil will appear brightly.

The proximal end of the distal end coil is threaded into the distal end of the proximal coil. The coils are joined into a unitary assembly by brazing. The brazing also secures the coils to the core wire. The brazing however, fills the space between the coils and the wire over a length of the reduced diameter portion. This consequently increases the effective diameter of the core wire abruptly, thus changing the core wire's flexibility at the braze or solder.

SUMMARY OF THE INVENTION

The present invention pertains generally to improved guide wire tips. These tips include various configurations of core wires, coils and radiopaque material to enhance their handling characteristics and visibility by reducing radioscopic means.

A guide wire tip in accordance with the preferred embodiment of the present invention includes a core wire having a proximal end and a distal end. The core wire includes a tapered portion proximate the distal end. The tapered portion has a transverse, cross-sectional area which generally decreases distally. A tip is disposed at the distal end of the guide wire. The tip has a transverse, cross-sectional area larger than the smallest transverse cross-sectional area of the tapered portion of the core wire. A coil extends over the core wire to the tip and extends over at least a portion of the tapered portion. A radiopaque sheath is disposed proximate the tip and between the core wire and the coil.

The coil can be radiopaque and formed from a material such as platinum. The sheath is preferably a radiopaque loaded heat shrink tube. The tip is atraumatically rounded at its distal end. The tip and/or core wire can be formed from stainless steel. The core wire can include a portion having a circular transverse cross section and a portion having a ribbon shaped transverse cross section proximate its distal end. A transition between the circular cross section portion and the ribbon portion can have a generally parabolic shape.

In yet another embodiment of a guide wire tip in accordance with the present invention, the core wire and tip can be as described above. First and second coils extend over the core wire. The first coil being proximate the tip and the second coil being proximal the first coil. A spacer is disposed between the coils. A low friction sleeve is disposed over at least a portion of the second coil.

At least one of the coils can be radiopaque. The sleeve preferably is formed from PTFE. The spacer can be generally radiotranslucent.

DETAILED DESCRIPTION OF THE PREFERRED EMBODIMENTS

Figure 1:
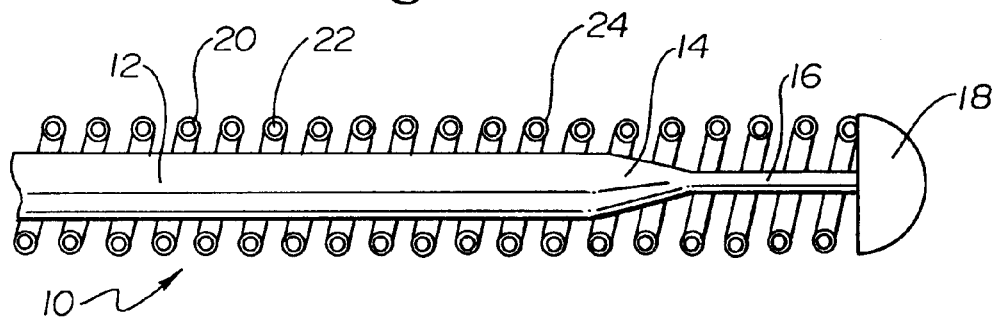
FIG. 1 is a longitudinal, cross-sectional view of the guide wire tip in accordance with the present invention.

Referring now to the drawings wherein like reference numerals refer to like elements throughout the several views, FIG. 1 is a longitudinal, cross-sectional view of the guide wire tip 10 in accordance with the present invention. Guide wire tip 10 includes a core wire 12 having a proximal end and a distal end, the former not being shown. Core wire 12 can be formed in diameters and lengths appropriate to the various percutaneous procedures conducted using guide wires. A generally parabolic shaped transition 14 can be made between a ribbon section 16 of core wire 12 and a generally circular transverse cross section proximal of transition 14.

A rounded atraumatic tip 18 is adhered to, soldered to or formed at the distal end of core wire 12. Surrounding the distal end of core wire 12 is a helical coil 20. Helical coil 20 includes an inner coil 22 having a highly radiopaque plating layer 24 deposited on its surface. Coil 20 preferably extends proximally to a point where the thickness of core wire 12 has been transitioned to have a diameter approximately equal to the inside diameter of coil 20. There coil 20 will be adhered to, soldered to or otherwise affixed to core wire 12.

Core wire 12 and tip 18 can be formed from stainless steel, Nitinol or other bio-compatible materials known to those skilled in the art. Inner coil 22 is preferably formed from stainless steel plated or ion deposited with a highly radiopaque metal layer 24 such as gold or platinum. It should be understood, however, that the materials recited herein are merely exemplary and one skilled in the art would know that alternative bio-compatible materials could be advantageously used.

Figure 2:
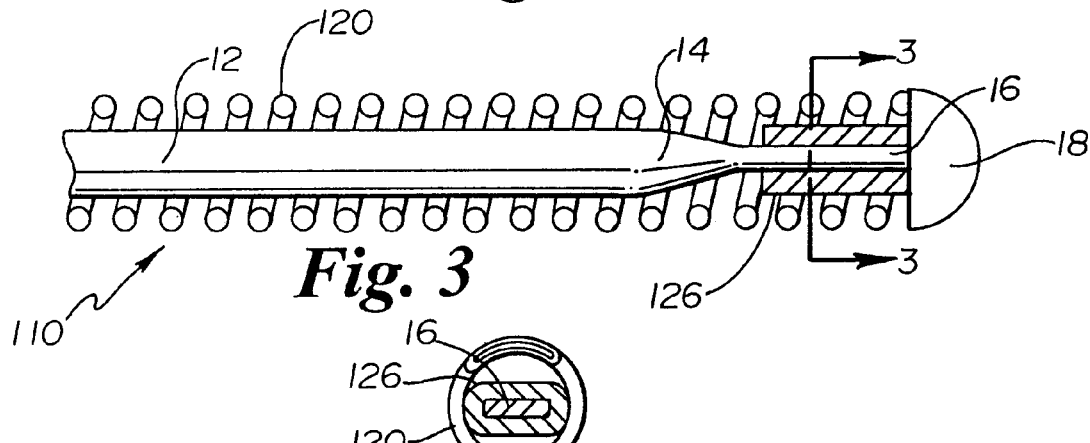
FIG. 2 is a longitudinal, cross-sectional view of another guide wire tip in accordance with the present invention.

FIG. 2 is a longitudinal, cross-sectional view of an alternate embodiment of a guide wire tip 110 in accordance with the present invention. Guide wire tip 110 can include a core wire 12 and tip 18 as described above. A helical coil 120 is disposed over core wire 12 in a manner similar to that of coil 20 described above. In the case of guide wire tip 110, however, core wire 120 is shown without a inner coil 22 and plate layer 24. Rather, a coil formed of a single material is shown. It can be understood, however, that coil 20 of tip 10 could be substituted for coil 120 on guide wire tip 110. Coil 120 is preferably formed from stainless steel, Nitinol, platinum or other bio-compatible material as known to those skilled in the art.

Disposed about the distal end of core wire 12 between coil 120 and core wire 12 is a substantially radiopaque sheath 126. Sheath 126 can be polymer shrink fit tube loaded with a heavy metal such as tungsten. The wire which forms coil 120 preferably has a rectangular cross-section.

Figure 3:
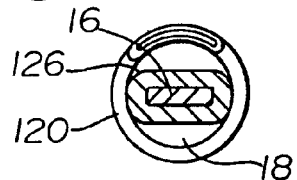
FIG. 3 is a transverse, cross-sectional view of the guide wire of FIG. 2.

FIG. 3 is a transverse, cross-sectional view of guide wire tip 110 of FIG. 2. The transverse, cross-sectional shape of ribbon portion 16 is apparent. Sheath 126 surrounds ribbon 16 between ribbon 16 and coil 120. Tip 18 is visible in the background, however the sheath could be formed to fill the space shown between ribbon 16 and coil 120.

Figure 4:
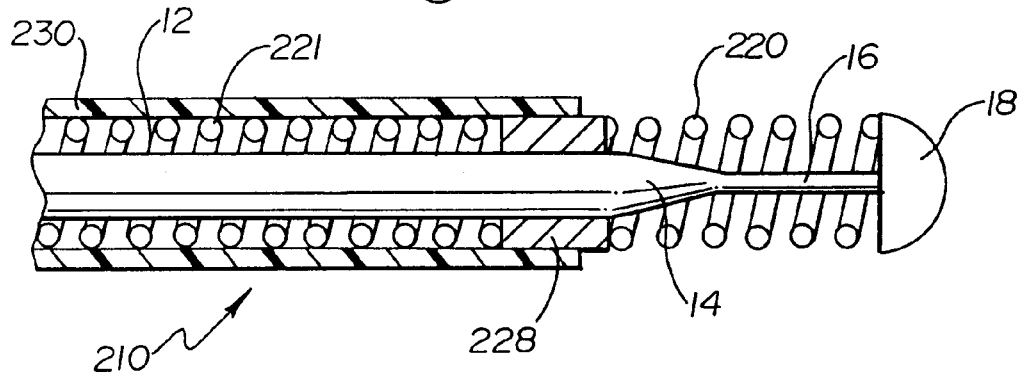
FIG. 4 is a longitudinal, cross-sectional view of yet another embodiment of the guide wire tip in accordance with the present invention.

FIG. 4 is a longitudinal, cross-sectional view of yet another embodiment of a guide wire tip 210 in accordance with the present invention. Core wire 12 and tip 18 of tip 210 is substantially similar to that as described above with respect to core wire 12 of guide wire tip 10. First and second coils 220 and 221 are disposed around core wire 12. First coil 220 is spaced from second coil 221 by spacer 228 disposed around core wire 12. A lubricous sheath 230 is disposed around second coil 221 and a portion of spacer 228.

Both coils 220 and 221 can be formed from a radiopaque material such as platinum or could be formed as coil 20 with an inner coil and a radiopaque plating. Sheath 230 is preferably PTFE. Spacer 228 can be formed from a heat shrink polymer and can be, but is not necessarily substantially radiotranslucent. The proximal end of coil 221 is connected to core wire 12 as described with respect to guide wire tip 10. The distal end of coil 221 and the proximal distal end of coil 220 can be connected to core wire 12 or tip 18 as the case may be by adhesive, solder or other suitable bonding material. It can be appreciated by those skilled in the art that various other bio-compatible materials are available for construction of the various elements of guide wire tip 210.

Numerous characteristics and advantages of the invention covered by this document have been set forth in the foregoing description. It will be understood, however, that this disclosure is, in many respects, only illustrative. Changes may be made in details, particularly in matters of shape, size, and arrangement of parts without exceeding the scope of the invention. The inventions's scope is, of course, defined in the language in which the appended claims are expressed.

What is claimed is:

1. A guide wire tip, comprising:

a core wire having a proximal end and a distal end, the core wire including a tapered portion, proximate the distal end, the tapered portion having a transverse cross-sectional area which generally decreases distally;

a distal portion of the core wire having a first transverse dimension greater than a second transverse dimension disposed perpendicularly to the first transverse dimension;

a tip disposed at the distal end of the core wire, the tip having a transverse cross-sectional area larger than the smallest transverse cross-sectional area of the tapered portion of the core wire;

a coil extending over the core wire to the tip, the coil extending over at least a portion of the tapered portion; and a radiopaque sheath comprised of a flexible polymeric material loaded with a radiopaque material: the radiopaque sheath overlaving the distal portion of the core wire.

2. The guide wire tip in accordance with claim 1, wherein the coil is radiopaque.

3. The guide wire tip in accordance with claim 2, wherein the coil includes platinum.

4. The guide wire tip in accordance with claim 1, wherein the sheath comprises a radiopaque loaded heat shrink tube.

5. The guide wire tip in accordance with claim 1, wherein the tip is atraumatically rounded at its distal end.

6. The guide wire tip in accordance with claim 5, wherein the tip comprises stainless steel.

7. The guide wire tip in accordance with claim 1, wherein the core wire comprises stainless steel.

8. The guide wire tip in accordance with claim 1, wherein the core wire includes a portion having a circular transverse cross section.

9. The guide wire tip in accordance with claim 8, wherein the core wire includes a portion having a ribbon-shaped transverse cross section.

10. The guide wire tip in accordance with claim 9, having a transition between the circular cross section portion and the ribbon portion which has a generally parabolic shape.

* * * * *